United States Patent [19]
Savage

[11] Patent Number: 6,113,594
[45] Date of Patent: Sep. 5, 2000

[54] SYSTEMS, METHODS AND APPARATUS FOR PERFORMING RESECTION/ABLATION IN A CONDUCTIVE MEDIUM

[75] Inventor: George M. Savage, Portola Valley, Calif.

[73] Assignee: Ethicon, Inc., Somerville, N.J.

[21] Appl. No.: 08/678,412

[22] Filed: Jul. 2, 1996

[51] Int. Cl.[7] .................................................. A61B 18/18
[52] U.S. Cl. .............................. 606/41; 606/48; 606/50; 128/898
[58] Field of Search ................................ 606/37, 39, 40, 606/41, 45, 46, 49, 52; 607/98, 99; 128/898; 604/22, 14

[56] References Cited

U.S. PATENT DOCUMENTS

| | | |
|---|---|---|
| 1,814,791 | 7/1931 | Ende . |
| 2,031,682 | 2/1936 | Wappler et al. ........................ 606/46 |
| 3,460,539 | 8/1969 | Anhalt . |
| 3,799,168 | 3/1974 | Peters . |
| 3,850,162 | 11/1974 | Iglesias ................................. 606/46 |
| 3,910,279 | 10/1975 | Okada et al. . |
| 3,987,795 | 10/1976 | Morrison . |
| 4,033,351 | 7/1977 | Hetzel . |
| 4,132,227 | 1/1979 | Ibe ........................................ 606/46 |
| 4,161,950 | 7/1979 | Doss et al. . |
| 4,228,800 | 10/1980 | Degler, Jr. et al. . |
| 4,314,559 | 2/1982 | Allen . |
| 4,333,467 | 6/1982 | Domicone . |
| 4,481,057 | 11/1984 | Beard . |
| 4,492,231 | 1/1985 | Auth . |
| 4,493,320 | 1/1985 | Treat . |
| 4,534,347 | 8/1985 | Taylor . |
| 4,545,375 | 10/1985 | Cline . |
| 4,589,411 | 5/1986 | Friedman . |
| 4,622,966 | 11/1986 | Beard . |

(List continued on next page.)

FOREIGN PATENT DOCUMENTS

1311726 A1  5/1987  U.S.S.R. .
WO 94/26228  11/1994  WIPO .

OTHER PUBLICATIONS

Brill, M.D., Andrew I., "What is the Role Hysteroscopy in the Management of Abnormal Uterine Bleeding?," *Clinical Obstetrics and Gynecology*, vol. 38, No. 2, Jun. 1995, pps: 319–345.

Goldrath, M.D., Milton H., "Hysteroscopic Endometrial Ablation," *Obstetrics and Gynecology Clinics of North America*, vol. 22, No. 3, Sep. 1995, pps: 559–571.

Garry, M.D., Ray, "Good Practice With Endometrial Ablation," *Obstetrics and Gynecology*, vol. 86, No. 1, Jul. 1995, pps: 144–150.

*Primary Examiner*—Linda C. M. Dvorak
*Assistant Examiner*—R. Kearney
*Attorney, Agent, or Firm*—Verne E. Kreger, Jr.

[57] ABSTRACT

The invention provides methods, systems and apparatus for electrosurgically treating tissue particularly within the uterus and prostate. In an exemplary method, a surgical instrument comprising an elongate shaft having a proximal end and a distal end, an active electrode near the distal end, and a return electrode is introduced into the uterus. An electrically conductive fluid is then introduced into the uterus to distend the uterus and to form an electrically conductive path between the active electrode and the return electrode. The active electrode is then contacted against tissue within the body cavity. Current is passed between the active electrode and the return electrode while the active electrode is contacting the tissue. The active electrode is provided with a surface area which is selected to produce a power density sufficient to resect or coagulate tissue. The active electrode is then moved along and through the tissue to remove, coagulate or vaporize the tissue.

16 Claims, 6 Drawing Sheets

U.S. PATENT DOCUMENTS

| | | | |
|---|---|---|---|
| 4,657,016 | 4/1987 | Garito et al. . | |
| 4,785,807 | 11/1988 | Blanch . | |
| 4,802,476 | 2/1989 | Noerenberg et al. . | |
| 4,905,691 | 3/1990 | Rydell . | |
| 4,936,842 | 6/1990 | D'Amelio et al. | 606/42 |
| 4,943,290 | 7/1990 | Rexroth et al. | 606/45 |
| 4,976,711 | 12/1990 | Parins et al. | 606/48 |
| 4,998,527 | 3/1991 | Meyer | 606/46 |
| 4,998,933 | 3/1991 | Eggers et al. . | |
| 5,013,312 | 5/1991 | Parins et al. . | |
| 5,035,696 | 7/1991 | Rydell . | |
| 5,035,969 | 7/1991 | Rydell | 606/47 |
| 5,080,660 | 1/1992 | Buelna | 606/45 |
| 5,178,620 | 1/1993 | Eggers et al. . | |
| 5,192,280 | 3/1993 | Parins . | |
| 5,197,964 | 3/1993 | Parins . | |
| 5,201,732 | 4/1993 | Parins et al. . | |
| 5,250,047 | 10/1993 | Rydell . | |
| 5,282,799 | 2/1994 | Rydell . | |
| 5,318,564 | 6/1994 | Eggers . | |
| 5,356,408 | 10/1994 | Rydell . | |
| 5,366,443 | 11/1994 | Eggers et al. | 604/114 |
| 5,395,363 | 3/1995 | Billings et al. . | |
| 5,417,697 | 5/1995 | Wilk et al. | 606/46 |
| 5,419,767 | 5/1995 | Eggers et al. . | |
| 5,456,689 | 10/1995 | Kresch et al. . | |
| 5,571,100 | 11/1996 | Goble et al. | 606/41 |
| 5,603,332 | 2/1997 | O'Connor | 128/716 |
| 5,681,282 | 10/1997 | Eggers et al. | 604/114 |
| 5,683,366 | 11/1997 | Eggers et al. | 604/114 |
| 5,685,877 | 11/1997 | Pagedas et al. | 606/46 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |

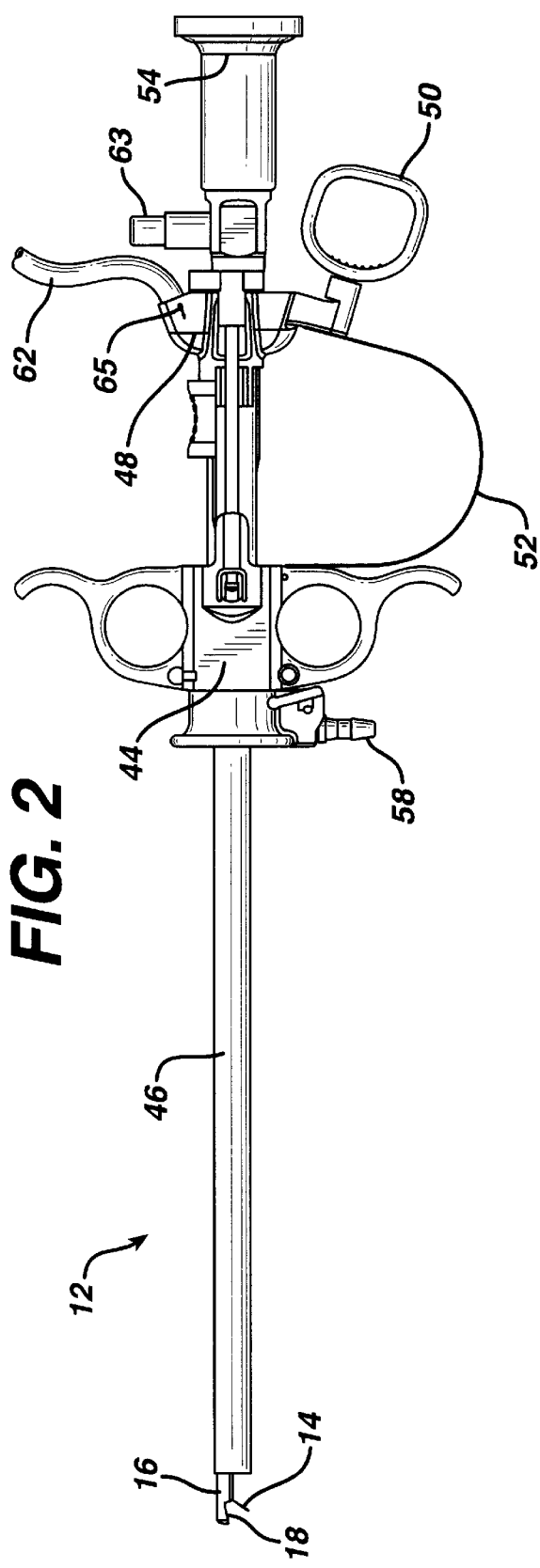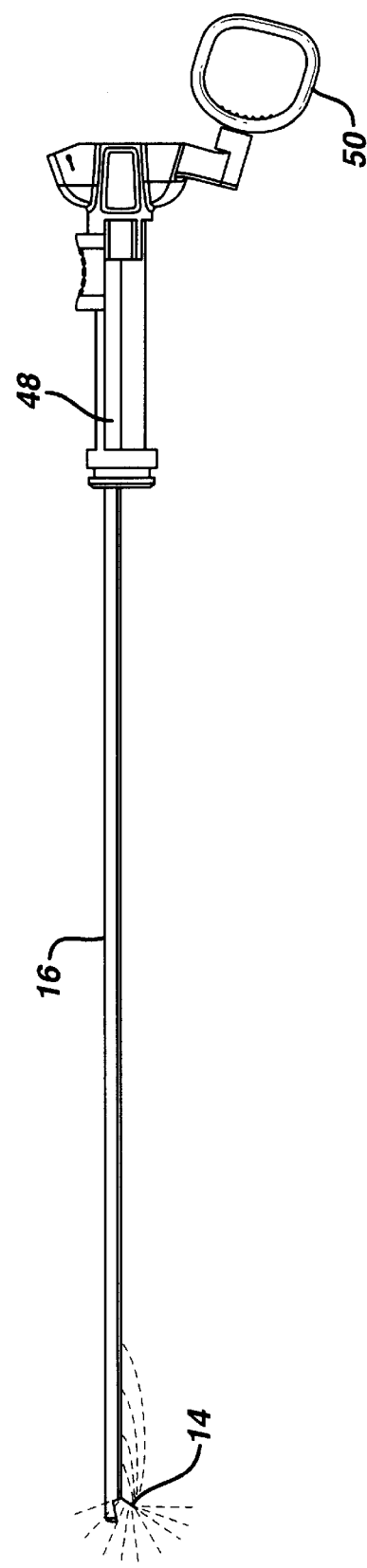

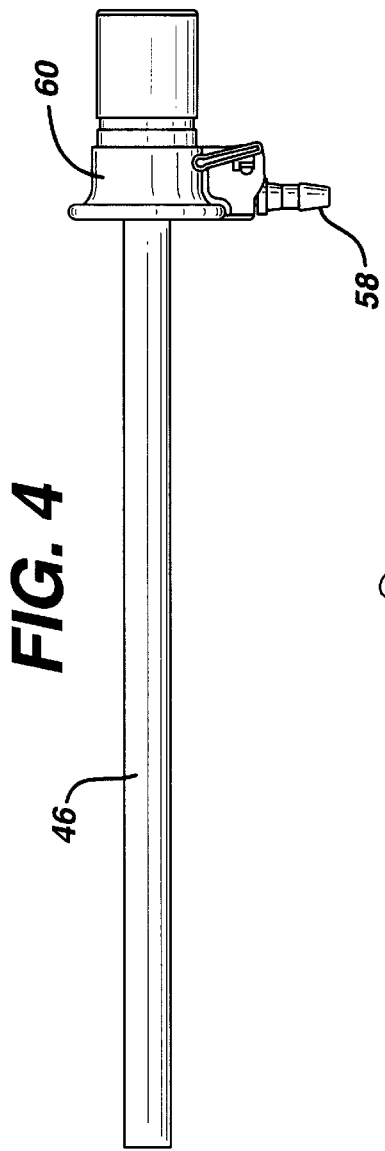
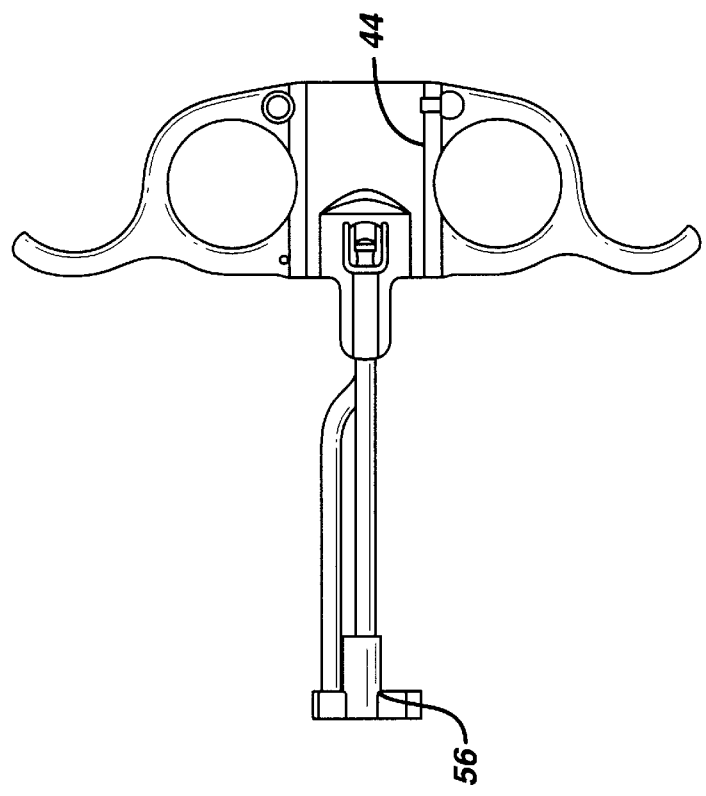
FIG. 4
FIG. 5

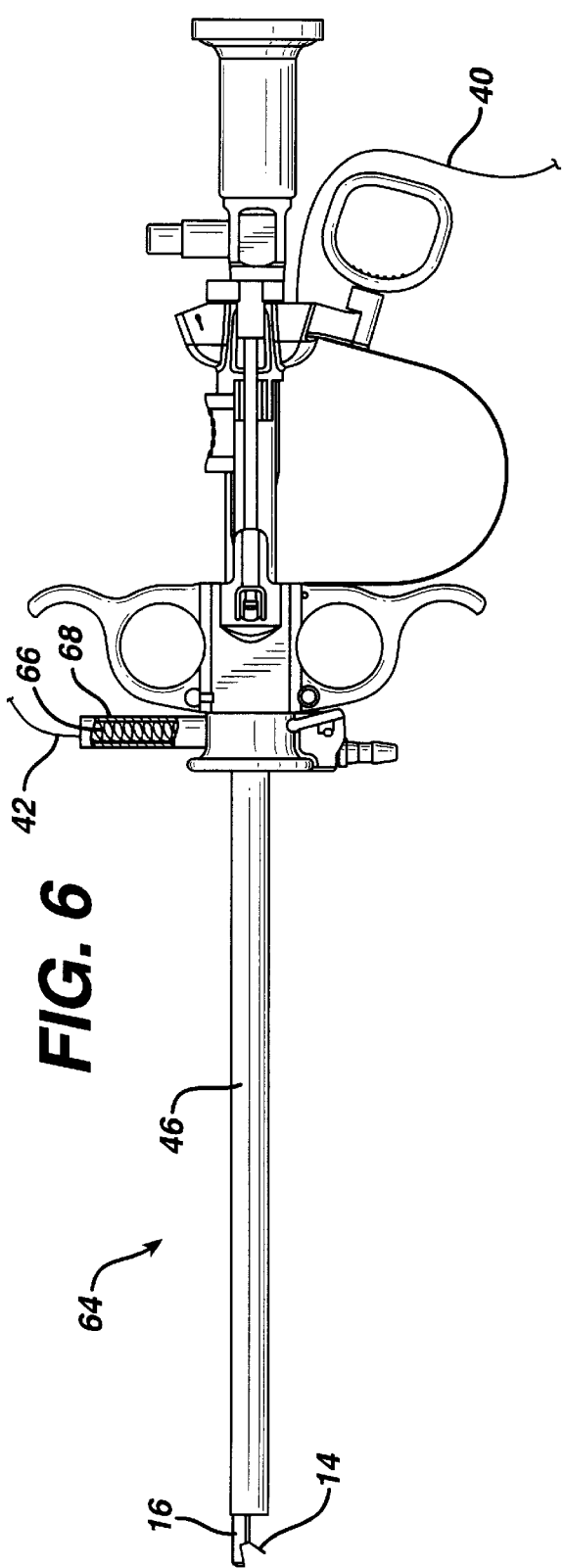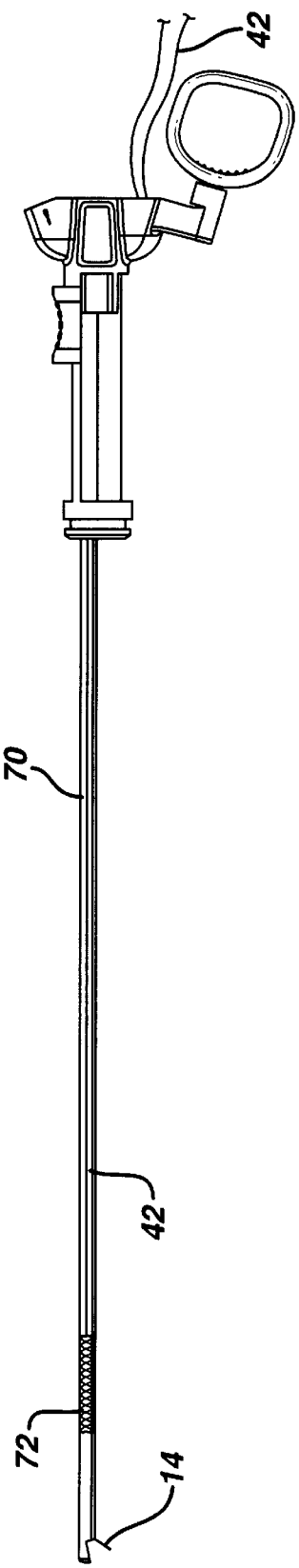

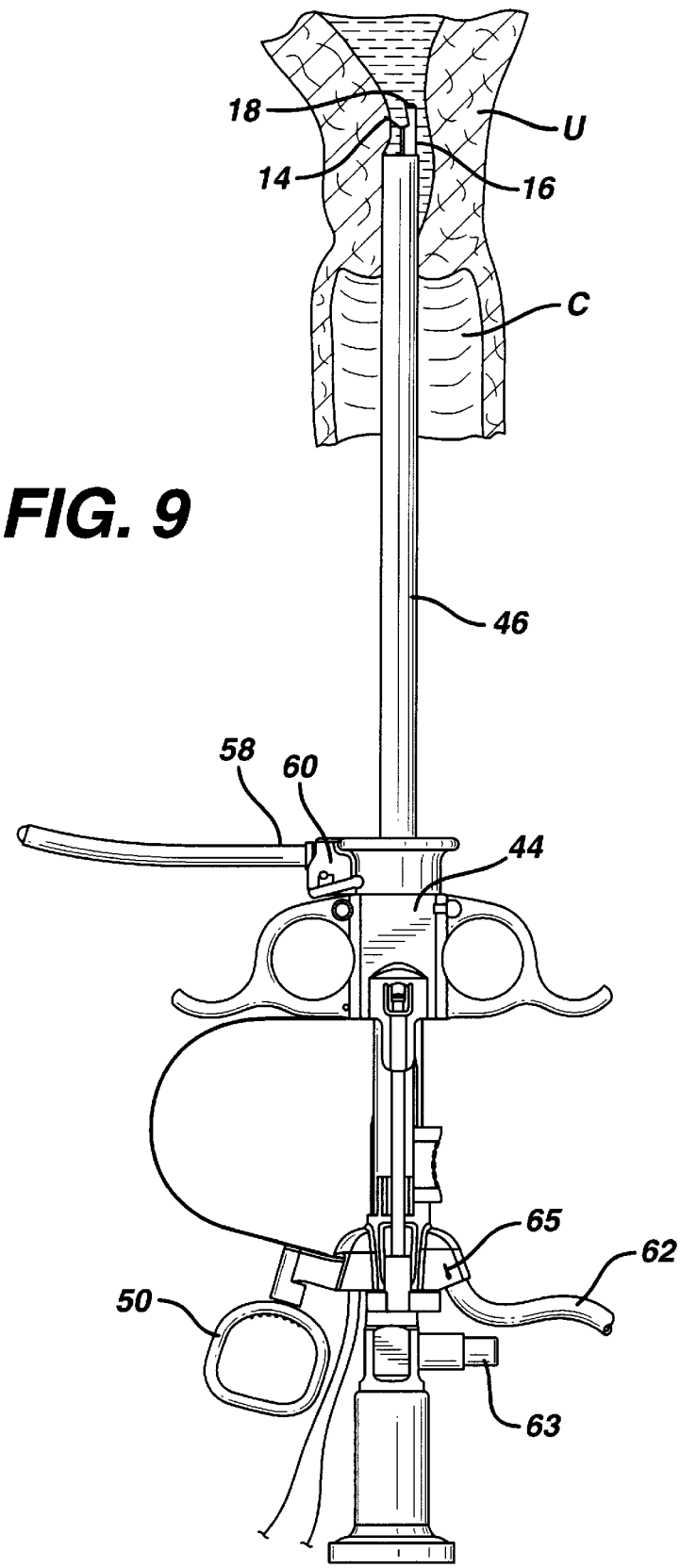

SYSTEMS, METHODS AND APPARATUS FOR PERFORMING RESECTION/ABLATION IN A CONDUCTIVE MEDIUM

BACKGROUND OF THE INVENTION

The invention relates generally to the field of electrosurgery, and more particularly to electrosurgical procedures which are performed within a body cavity which is filled or distended with a liquid. In one particular aspect, the invention relates to electrosurgical procedures for performing endometrial ablation and resection.

Electrosurgical procedures have become widely used to treat a variety of ailments including those associated with the uterus, such as uterine wall resection, endometrial ablation, endometrial resection, submucous myoma resection, intramural myoma resection, transmural myoma resection, and resection of the cervix and the cervical canal. Other electrosurgical procedures include kidney resection (laparoscopy), prostate resection (cystoscopy), ovary resection, removal of lung tissue and tumors (thoracoscopy), and the like. Of these electrosurgical procedures, those dealing with the treatment of the uterus are of particular interest.

Menorrhagia, or abnormal uterine bleeding, is a frequent clinical problem encountered by gynecologists. One common procedure for dealing with such abnormal bleeding is through the performance of a hysterectomy. In the United States, it is estimated that about 650,000 hysterectomies are performed each year. However, the performance of hysterectomies is becoming more and more undesirable, especially as new techniques and procedures have been developed to treat abnormal bleeding in a less intrusive manner. For example, a recent development is the use of hysteroscopic surgery employing laser or high frequency electrosurgical energy to destroy or remove the endometrium and a portion of the myometrium using direct visualization. Such procedures have been effective in significantly reducing menstrual blood flow and in decreasing secondary dysmenorrhea. For example, one exemplary device and method for performing both endometrial resection and ablation is described in U.S. Pat. No. 5,456,689, the disclosure of which is herein incorporated by reference. Other exemplary resection/ablation devices are described in copending U.S. application Ser. Nos. 08/322,680, filed Oct. 13, 1994, (attorney docket number 16944-00110); and 60/008,225, filed Nov. 8, 1995 (attorney docket no. 16944-001200), the complete disclosures of which are herein incorporated by reference.

Such electrosurgical resection/ablation devices are usually configured to employ monopolar current when used within an open body cavity, such as the uterus. With monopolar current, the cutting or ablation surface usually consists of an active electrode and a conductive pad return electrode which is applied to the patient's skin. Hence, the current flowing from the active electrode disperses into a low current field which terminates in the return electrode. The return electrode is large enough to reduce the current density to a level that is low enough to prevent the skin from becoming injured (burned) by the return current. Although small, there is some risk that the cutting current traveling from the inside wall of the uterus to the return pad could become concentrated in some delicate tissue, such as the bowel, which happens to be touching the outside of the uterus.

Another concern with the use of electrosurgical procedures within a body cavity such as the uterus is that the body cavity usually needs to be distended so that the desired tissue may be adequately visualized and so that enough room is provided to manipulate the surgical instrument. To distend the uterus, an electrically insulated fluid is generally employed. Common non-conductive distention fluids include Sorbitol, Glycine, Sorbitol-Mannitol or Mannitol. However, such fluids can in certain circumstances pose a danger to the patient. For example, if excessive quantities are absorbed into the patient's circulation, pulmonary edema may result. Further, since such fluids are electrolyte-free, they will, when absorbed in excess, produce plasma dilution of sodium, potassium and other electrolytes. This in turn may produce cardiac problems. Such a fluid may also cause water to transfer into brain cells, producing cerebral edema. Finally, Glycine is metabolized in the body and broken down into ammonia. Such a toxic substance can produce disturbances of consciousness, coma, or even death.

To avoid the risk of such complications, fluid loss (the difference between distention fluid used and fluid recovered from the procedure) is carefully monitored during the procedure and distention pressure is controlled to the minimum required for visualization. Such procedures are described in, for example, copending U.S. application Ser. No. 60/006,408, filed Nov. 9, 1995 (attorney docket no. 16944-000710), the disclosure of which is incorporated herein by reference.

The use of electrolyte solutions to distend the uterus have generally been dismissed for use with electrosurgery since the high frequency current is dispensed in all directions and thereby reduces the possibility of obtaining coagulation or cutting at the tissue/electrode interface. More specifically, when radio frequency current is used within an environment containing a non-conductive fluid, the current supplied to the active electrode passes directly into the tissue contacting the electrode, rather than through the non-conductive fluid. Hence, the power is dissipated within the body in a generally hemispherical pattern. Moreover, since current is delivered through only a portion of the active electrode, the current density at the active electrode is sufficient to resect or coagulate tissue. When the non-conductive fluid is replaced with a conductive fluid, the power supplied at the active electrode dissipates in a generally spherical pattern. This in turn reduces the current density at the active electrode so that effective resection or coagulation cannot occur.

Hence, for these and other reasons, it would be desirable to provide systems, methods and apparatus which would provide a safer environment when using electrosurgical procedures, particularly in combination with a distention fluid. Such systems, methods and apparatus should reduce or eliminate the risks associated with the use of nonconductive distention fluids. The systems, methods and apparatus should further prevent or reduce the possibility of unwanted current buildup within the body.

SUMMARY OF THE INVENTION

The invention provides systems, methods and apparatus for increasing patient safety during electrosurgical procedures. The systems, methods and apparatus will be particularly useful in performing electrosurgical procedures within a body cavity or organ, such as the uterus or prostate, which is distended with a distention fluid. According to one exemplary method, a surgical instrument is introduced into the uterus. The surgical instrument comprises an elongate shaft having a proximal end and a distal end, an active electrode near the distal end, and a return electrode. The active electrode is provided with a surface area which is selected to produce a current density sufficient to resect or coagulate tissue. An electrically conductive fluid is also introduced into the uterus to distend the uterus and to form an electrically conductive path between the active electrode and the return electrode. The active electrode is contacted against tissue within the uterus and current is passed between the active electrode and the return electrode while the active electrode is contacting the tissue. The active electrode is then moved along and through the tissue to remove, coagulate or vaporize the tissue.

In one aspect, the active electrode will preferably comprise a wire loop having a diameter in the range from about 3 mm to about 12 mm. The wire loop may optionally be provided with rotating spurs or "stars" to provide enhanced coagulation. The return electrode is preferably positioned proximal to the active electrode at a location which is selected so that power produced at the active electrode is dissipated in a focused non-spherical pattern, i.e. in a direction which tends to focus on or move directly toward the return electrode rather than proceeding in a spherical pattern. In this manner, a greater level of current density will be provided in the tissue surrounding the tissue/electrode interface.

In one particularly preferable aspect of the method, the electrically conductive fluid comprises an isotonic irrigation fluid. In another aspect of the method, the surgical instrument further includes the morcellator so that tissue removed by the active electrode may be morcellated. Once morcellated, the tissue will preferably be aspirated through the elongate shaft. In a further aspect, the electrically conductive fluid will preferably be introduced into the body cavity through the elongate shaft.

The return electrode may be configured in a variety of ways and may comprise, for example, a pad that is attached to the elongate shaft proximal to the active electrode, a wire coil, the elongate shaft itself, a roller, and the like. In this manner, current dispersed from the active electrode will pass through the electrically conductive fluid and to the return electrode, which in turn is attached to the surgical instrument. Placement of the return electrode within the body cavity is advantageous in that it reduces the power dissipation within the conductive fluid, thereby increasing the amount of current in the vicinity of the electrode/tissue interface. Further, when within the body cavity the return electrode will help prevent the concentration of current in unwanted areas. Moreover, by using an electrically conductive fluid, patient safety and comfort is improved by reducing the chance for alteration of the electrolyte balance and/or osmolarity of the blood.

The invention further provides an exemplary system for surgically treating tissue, particularly within the uterus or prostate. The system comprises a surgical instrument having an elongate shaft with a proximal end and a distal end, an active electrode near the distal end, and a return electrode. The system further includes an electrically conductive fluid which may be introduced into a body cavity to form an electrically conductive path between the active electrode and the return electrode when within the body cavity. The active electrode has a surface area which is selected to produce a current density sufficient to resect or coagulate tissue. Further, the return electrode is positioned proximal to the active electrode at a location selected so that the power produced at the active electrode is dissipated in a focused non-spherical pattern.

In one preferable aspect, the electrically conductive fluid comprises an isotonic irrigation fluid. In another aspect, the surgical instrument preferably includes a morcellator for morcellating tissue removed by the active electrode. In still a further aspect, a lumen is disposed through the elongate shaft and an aspiration source is provided for aspirating removed tissue through the elongate shaft. In yet another aspect, the electrically conductive fluid may be introduced into the body cavity through the lumen in the shaft.

The surgical instrument may optionally be provided with a telescope which is operably attached to the shaft so that the active electrode may be visualized through the scope. Optionally, ultrasound may be employed for visualizing tissue within the body cavity. The return electrode will preferably be operably attached to the elongate shaft proximal to the active electrode and may comprise a wire coil, a pad on the elongate shaft, or the elongate shaft itself. The active electrode will preferably comprise a wire loop having a diameter in the range from about 3 mm to about 12 mm.

The invention still further provides an exemplary surgical instrument comprising an elongate shaft having a proximal end and a distal end. An active electrode is operably attached to the shaft near the distal end. A passive return electrode is operably attached to the shaft at a location which is spaced apart from the active electrode. The active electrode has a surface area which is selected to produce a current density sufficient to resect, coagulate or vaporize tissue. Further, the return electrode is positioned proximal to the active electrode at a location selected so that the power produced at the active electrode is dissipated into a much larger surface area as compared to the active electrode.

In one preferable aspect, the surface area of the active electrode is much less than the surface area of the passive return electrode so that a greater current density is produced at the active surface relative to the passive surface. In this manner, a current density sufficient to cut or coagulate tissue will only be generated at the active electrode. As the current is dispersed from the active electrode, it passes to the return electrode and is sufficiently dispersed to provide a safe current density within the body cavity. Further, by including the return electrode within the body cavity, an electrically conductive distention fluid may be used within the body cavity.

Preferably, the passive return electrode is formed on the elongate shaft, or may alternatively comprise the shaft itself. The active electrode preferably comprises a wire loop having a diameter in the range from about 3 mm to about 12 mm. The wire loop may optionally be provided with rotating spurs or "stars" to provide enhanced coagulation.

BRIEF DESCRIPTION OF THE DRAWINGS

FIG. 2 is a side view of an exemplary electrosurgical device of the system of FIG. 1.

FIG. 3 is a side view of the body of the device of FIG. 2 having its sheath removed.

FIG. 4 is a side view of the sheath of the device of FIG. 2.

FIG. 5 is a side view of the handle of the device of FIG. 2.

FIG. 6 illustrates an alternative embodiment of the device of FIG. 2 having a coil as the return electrode according to the present invention.

FIG. 7 illustrates an alternative embodiment of the morcellator shaft of the device of FIG. 2 having a return electrode pad thereon according to the present invention.

FIG. 9 illustrates the device of FIG. 2 being used to electrosurgically treat the uterus when distended with an electrically conductive fluid according to the present invention.

DETAILED DESCRIPTION OF THE SPECIFIC EMBODIMENTS

The invention provides methods, systems and apparatus for electrosurgically treating tissue. The methods, systems and apparatus will preferably be used to treat tissue located within a body cavity or organ that is filled or distended with a distention fluid. Although useful in a variety of body cavities or organs, such as the prostate and the bladder, the invention will find its greatest use in electrosurgically treating the endometrial lining of the uterus.

The distention medium will preferably comprise an electrically conductive fluid such as saline, Ringer's Lactate Solution, or the like which do not significantly alter the electrolyte balance of the blood. In this manner the risk of cerebral edema, and other risks which may arise if the distention medium passes into the blood stream can be greatly reduced or eliminated.

Apparatus according to the invention will, in one preferable aspect, comprise an active electrode such as an electrosurgical cutting wire or loop, and may include ablation spurs or "stars" as described in copending U.S. application Ser. No. 60/008,225, previously incorporated by reference. The device will further include a "passive" return electrode which is preferably attached to the electrosurgical instrument so that it is also within the body cavity during treatment. The return electrode will preferably have a surface area that is substantially greater than the surface area of the active electrode so that the current density level at the return electrode is significantly less than at the active electrode. Moreover, the return electrode is preferably positioned proximal to the active electrode at a location selected so that power produced at the active electrode is dissipated in a pattern which is intended to approximate a focused power dissipation pattern where the dissipated power travels in a direction which is directed toward the return electrode rather than proceeding in a spherical pattern. In this manner, highly concentrated current will be produced at the active electrode/tissue interface so that cutting and/or ablation may occur at the active electrode. Higher current densities are also provided at the tissue/electrode interface by reducing the size of the active electrode. Preferably, the active electrode will comprise a wire loop having a diameter in the range from about 3 mm to about 12 mm.

The current that is dispersed into the conductive distention fluid concentrates on the return electrode. Due to the large surface area of the return electrode, the return current has the low enough current density so that it will not cut, coagulate, or otherwise harm tissue located within the body cavity.

Figure 1:
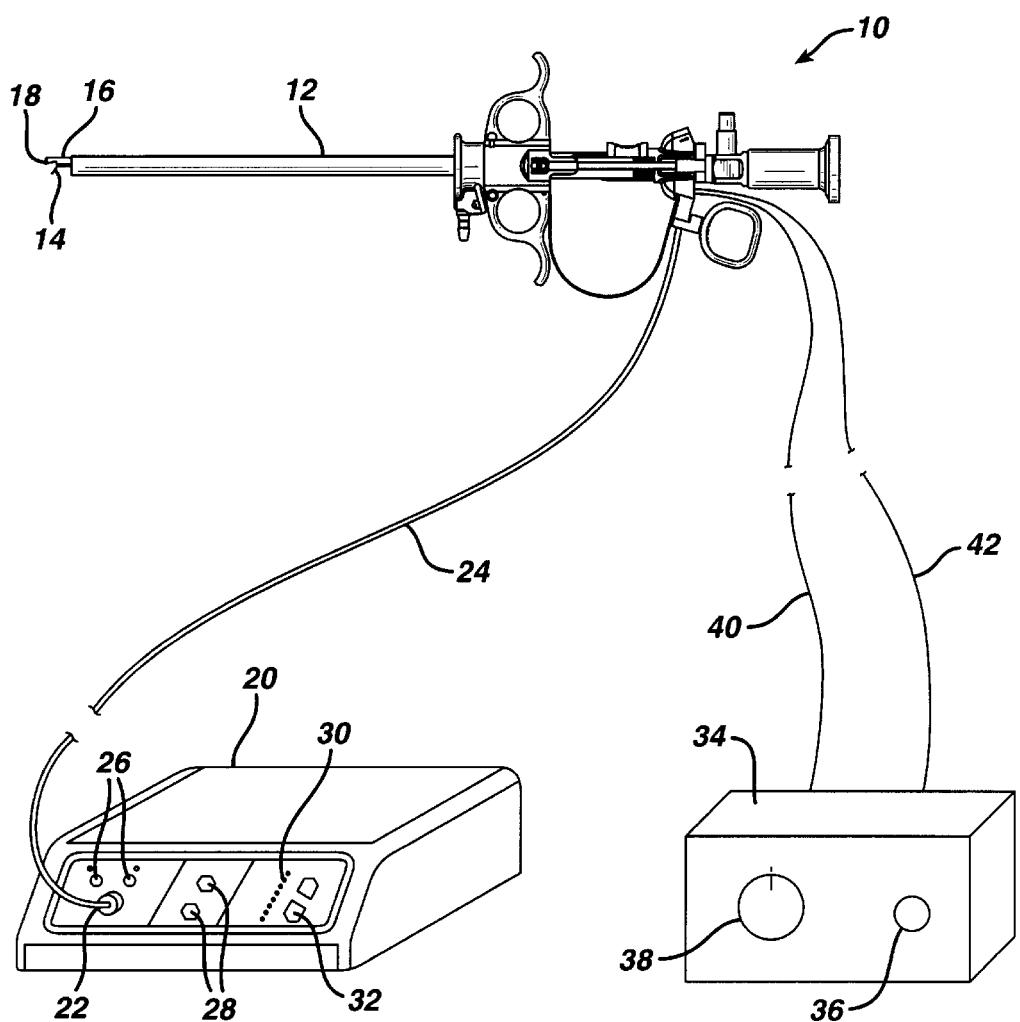
FIG. 1 illustrates an exemplary system for electrosurgically treating tissue in an environment having an electrically conductive fluid according to the present invention.

Referring now to FIG. 1, an exemplary system 10 for electrosurgically treating tissue will be described. System 10 includes a surgical instrument 12 for electrosurgically treating tissue and will be described in greater detail hereinafter. Briefly, surgical instrument 12 includes an active electrode 14 which may be used to cut and/or ablate tissue, and a morcellator shaft 16 having a morcellator 18 which is spaced apart from active electrode 14. A drive unit 20 is provided to rotate morcellator shaft 16. Drive unit 20 includes a variety of controls including a drive cable output 22 for connection to a drive cable 24, directional control switches 26, enable/stop switches 28, LED readout switches 30, and speed control switches 32. System 10 further includes an electrosurgery generator unit (ESU) 34 which supplies high frequency electrical current to active electrode 14. ESU 34 includes an enable switch 36 and a power control switch 38. Current is supplied to active electrode 14 through a line 40, while a line 42 provides a return path back to ESU 34.

Referring now to FIGS. 2 and 3, construction of surgical instrument 12 will be described in greater detail. As previously described, surgical instrument 12 includes active electrode 14 and morcellator shaft 16. Active electrode 14 is fashioned in the form of a wire loop which is in electrical communication with line 40 (See FIG. 1). Wire loop may optionally be provided with spurs, stars, cylinders, or the like which may be rotated as described in co-pending application Ser. No. 60/008,225 to enhance coagulation. Electrode 14 preferably has a diameter in the range from about 3 mm to about 12 mm. Morcellator shaft 16 has a lumen extending therethrough so that tissue removed by morcellator 18 may be aspirated through the lumen. Surgical instrument 12 further includes a handle 44 which provides a convenient grip for the surgeon. A sheath 46 which is preferably non-conductive provides a protective cover for morcellator shaft 16.

Morcellator shaft 16 is attached to a resector body 48 having a thumb ring 50. Thumb ring 50 and handle 44 cooperate together to axially translate active electrode 14. More specifically, a return spring 52 is placed between handle 44 and thumb ring 50 to bias thumb ring 50 away from handle 44. As the surgeon squeezes thumb ring 50 toward handle 44, active electrode 14 is translated forward. As the surgeon relaxes his hand, thumb ring 50 is slowly translated away from handle 44 with assistance from return spring 52 to slowly translate active electrode 14 back toward handle 44. A telescope 54 is conveniently provided to allow viewing of active electrode 14 during the procedure. As best shown in FIG. 5, handle 44 includes a scope mount 56 for holding scope 54. Optionally, an ultrasonic transducer may be employed along with telescope 54 (or in some cases may be used in place of telescope 54) to visualize tissue within the body cavity. Use of ultrasound is described in copending application Ser. No. 08/322,680, previously incorporated by reference. As shown in FIG. 2, a light cable 63 is provided for connecting a light source to telescope 54 so that the body cavity may be illuminated.

As shown in FIG. 3, surgical instrument 12 employs morcellator shaft 16 as the return electrode. By having electrode 14 extend from shaft 16, power produced at a distal portion of electrode 14 dissipates distally outward in a focused non-spherical pattern into the uterine tissue. As shown in phantom line, current leaving a proximal portion of active electrode 14 passes through the electrically conductive medium in a generally direct line where it concentrates on the entire morcellator shaft 16. In this manner, the amount of power dissipated into the conductive irrigation solution is reduced so that as electrode 14 is proximally translated through tissue, the proximal portion in contact with the tissue will have a current density sufficient to cut or coagulate the tissue. Due to the large surface area of morcellator shaft 16, the current density at morcellator shaft 16 will be at a safe level so that if morcellator shaft 16 engages tissue, the tissue will not be harmed. Morcellator shaft 16 is constructed of an electrically conductive material such as stainless steel, and is in electrical communication with return line 42 (See FIG. 1). Alternatively, surgical instrument 12 could be constructed so that sheath 46 serves as the passive return electrode. However, sheath 46 will preferably be non-conductive to maximize patient safety.

As best shown in FIGS. 2 and 4, surgical instrument 12 includes an irrigation connector 58 through which the electrically conductive media is introduced into the body cavity. An inflow valve 60 may be employed to control the volume of fluid flowing into the body cavity. When the body cavity is sufficiently distended, inflow valve 60 may be closed to maintain the fluid pressure within the body cavity. As shown in FIG. 2, a fluid tube 62 is provided on surgical instrument 12 and is in fluid communication with the lumen extending through morcellator shaft 16 so that morcellated tissue can be aspirated from the body cavity. A stopcock valve having a handle 65 is provided for preventing the flow of fluid through tube 62.

Referring now to FIG. 6, an alternative embodiment of a surgical instrument 64 will be described. Surgical instrument 64 is essentially identical to surgical instrument 12 of FIG. 2 except for the configuration of the passive return electrode. More specifically, surgical instrument 64 includes a return electrode 66 which is constructed in the form of a wire coil. Return electrode 66 is held within a non-conductive housing 68 which is attached to the instrument opposite irrigation connector 58. Return line 42 is connected to return electrode 66 to complete the electrical circuit. As configured, electrical current from active electrode 14 passes through the electrically conductive medium and concentrates on return electrode 66 where the current density is sufficiently small so that it will not harm surrounding tissue.

Referring to FIG. 7, an alternative embodiment of a morcellator shaft 70 for use with surgical instrument 12 will be described. Morcellator shaft 70 is essentially identical to morcellator shaft 16 of FIG. 3 except that morcellator shaft 70 includes a dispersive pad 72 attached thereto in the vicinity of active electrode 14. Preferably, pad 72 will be located within about 5 mm to about 50 mm of electrode 14. Return line 42 is in electrical communication with dispersive pad 72 allowing dispersive pad 72 to function as the passive return electrode. In this manner, current leaving active electrode disperses through the conductive medium and concentrates on dispersive pad 72 where the current density is sufficiently low to provide a safe working environment. Further, the distance between pad 72 and electrode 14 is selected such that the power dissipated within a conductive distention fluid will concentrate on pad 72 to form a focused non-spherical dissipation pattern. In this way, a higher level of current is provided at the tissue/electrode interface.

Figure 8:
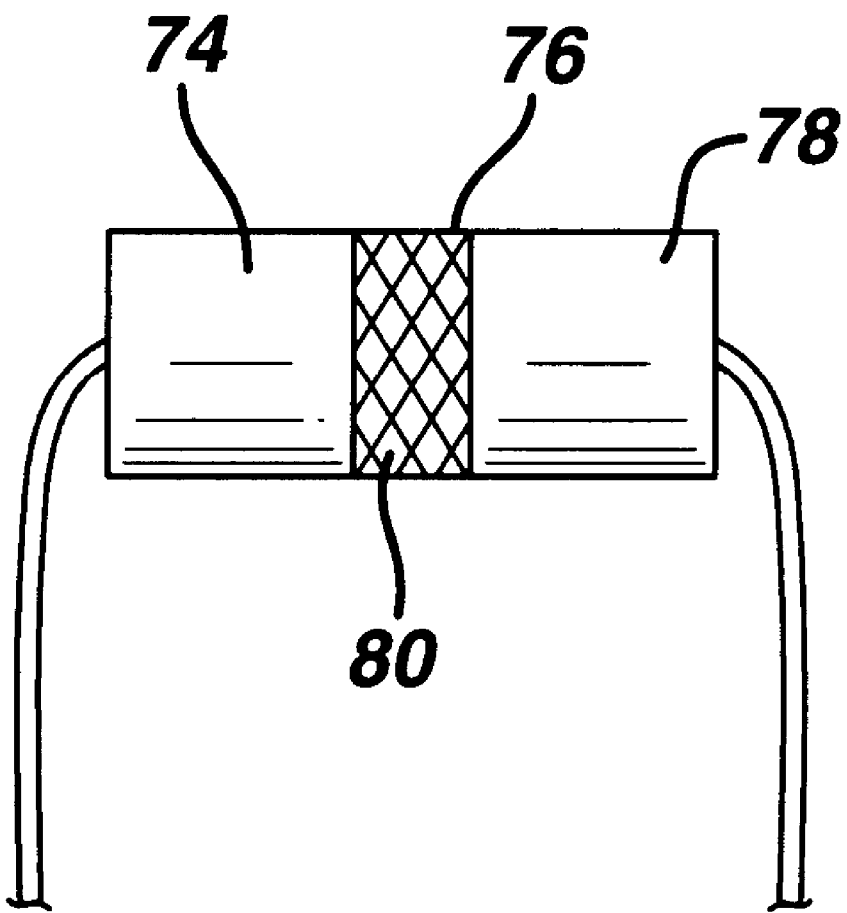
FIG. 8 illustrates a roller ball having an active electrode and a return electrode which may be used in an electrically conductive fluid according to the present invention.

Referring to FIG. 8, an alternative embodiment of an active electrode 74 will) be described. Active electrode 74 is included on a roller 76 which in turn includes a return electrode 78. Electrodes 74 and 78 are separated by an insulating spacer 80. The surface area of active electrode 74 and return electrode 78 are approximately equal so that the current densities at both the active electrode 74 and return electrode 78 will be approximately the same. To treat tissue, roller 76 is rolled along the tissue with electrodes 74 and 78 ablating the contacted tissue. One particular advantage of roller 76 is that it may operate in both an insulating and an electrically conductive distention medium. Roller 76 will conveniently be attached to a shaft (not shown) and may be provided with irrigation and aspiration sources similar to those previously described with surgical instrument 12.

An alternative electrosurgical device which may be used in an electrically conductive medium comprises a pair of closely spaced needle electrodes. Such a device is operated in a bipolar manner, with the current passing between the two needles. A ball may optionally be provided on each of the needles to control the depth of the needles within the tissue.

Referring now to FIG. 9, an exemplary method for performing endometrial resection/ablation with surgical instrument 12 will be described. Initially, sheath 46 is introduced to the uterus U through the cervical canal C with an obturator (not shown). The obturator is then removed and morcellator shaft 16 is introduced through sheath 46 until active electrode 14 and morcellator 18 are exposed within the uterus U. Inflow valve 60 is then opened and an electrically conductive irrigation fluid is delivered through irrigation connector 58. The uterus U is filled with the distention fluid until the uterus U is sufficiently distended. Electrical current is then provided to active electrode 14 whereupon active electrode 14 is translated back and forth by manipulating handle 44 and thumb ring 50 as previously described. Active electrode 14 is moved along and through tissue to remove and/or ablate the endometrial lining. Any removed tissue is chopped into smaller morsels by morcellator 18. The morsels in turn are removed through morcellator shaft 16 through tube 62. As fluid is withdrawn through tube 62, new fluid is introduced so that the uterus U maintains its distended configuration. To monitor the amount of fluid within the uterus U, a flow device, such as that described in copending U.S. application Ser. No. 60/006,408, previously incorporated by reference, may be used.

When distending the uterus with the electrically conductive fluid, a safer working environment is provided since the body can more safely handle the absorption of the electrically conductive fluid. Moreover, by employing morcellator shaft 16 as the return electrode, a safe working environment is provided with the uterus since the current leaving active electrode 14 will be dispersed through the electrically conductive fluid and will concentrate on shaft 16, rather than propagating through surrounding organs or tissue, such as the bowel, en route to a dispersive electrode located on the skin. In the event that shaft 16 inadvertently touches tissue, the current density will be sufficiently low so that such tissue will not be harmed. Moreover, by employing an active electrode with a relatively small surface area and a return electrode proximal to the active electrode, a high level of current is produced at the active electrode so that tissue surrounded by a conductive medium may effectively be resected and/or coagulated.

Another advantage of employing the morcellator as a return electrode is that both the inner and outer surfaces of the return electrode are in contact with the electrically conductive fluid. In this manner, the effective surface area of the return electrode is increased.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A method for surgically treating the uterus, the method comprising:

introducing a surgical instrument comprising an elongate shaft having a proximal end and a distal end, an active electrode near the distal end, and a return electrode into the uterus;

introducing an electrically conductive fluid into the uterus sufficient to distend the uterus and to submerse the active electrode and return electrode in the electrically conductive fluid to form an electrically conductive path between the active electrode and the return electrode;

contacting the active electrode against tissue within the uterus;

passing current between the active electrode and the return electrode while the active electrode is contacting the tissue, wherein the active electrode has a surface area which is selected to produce a current density sufficient to resect or coagulate the tissue; and moving the active electrode along and through the tissue to resect, coagulate or vaporize the tissue.

2. A method as in claim 1, wherein the active electrode comprises a wire loop having a diameter in the range from about 3 mm to about 12 mm, and wherein the return electrode is positioned proximal to the active electrode and further comprising moving the wire loop along and through the tissue.

3. A method as in claim 1, wherein the electrically conductive fluid comprises an isotonic irrigation fluid and further comprising passing the current through the isotonic irrigation fluid.

4. A method as in claim 1, wherein the surgical instrument includes a morcellator disposed proximal to the active electrode, and further comprising morcellating the tissue treated by the active electrode with the morcellator.

5. A method as in claim 4, further comprising aspirating the removed tissue through the elongate shaft.

6. A method as in claim 1, further comprising introducing the electrically conductive fluid into the uterus through the elongate shaft.

7. A method as in claim 1, wherein the return electrode comprises the elongate shaft and further comprising passing the current between the active electrode and the shaft.

8. A method for performing surgery within the uterus, the method comprising:

introducing a surgical instrument comprising an elongate shaft having a proximal end and a distal end, an active electrode near the distal end, and a proximal return electrode into the uterus;

introducing an electrically conductive fluid into the uterus sufficient to distend the uterus and to submerse the active electrode and return electrode in the electrically conductive fluid to form an electrically conductive path between the active electrode and the return electrode;

contacting the active electrode against tissue lining the uterus;

passing current between the active electrode and the return electrode while the active electrode is contacting the tissue, wherein power generated at the active electrode is dissipated in a focused non-spherical pattern within the uterus; and moving the active electrode along and through the tissue to resect, coagulate or vaporize tissue lining the uterus.

9. A method as in claim 8, wherein the electrically conductive fluid comprises an isotonic irrigation fluid and further comprising passing the current through the isotonic irrigation fluid.

10. A method as in claim 9, wherein the surgical instrument includes a morcellator, and further comprising morcellating the tissue treated by the active electrode.

11. A method as in claim 9, further comprising aspirating the removed tissue through the elongate shaft.

12. A method as in claim 9, further comprising introducing the electrically conductive fluid into the body cavity through the elongate shaft.

13. A method as in claim 9, wherein the return electrode comprises the elongate shaft and further comprising passing the current between the active electrode and the shaft.

14. A method for surgically treating a body organ, the method comprising:

introducing a surgical instrument comprising an elongate shaft having a proximal end and a distal end, an active electrode near the distal end, and a return electrode into the body organ;

introducing an electrically conductive fluid to distend the body organ and to submerse the active electrode and return electrode in the electrically conductive fluid to form an electrically conductive path between the active electrode and the return electrode;

contacting the active electrode against tissue within the body organ;

passing current between the active electrode and the return electrode while the active electrode is contacting the tissue and while the electrically conductive fluid surrounds the active electrode and the return electrode, wherein the active electrode has a surface area which is selected to produce a current density sufficient to resect, coagulate or vaporize the tissue; and moving the active electrode along and through the tissue to resect, coagulate or vaporize the tissue.

15. A method as in claim 14, wherein the body organ comprises the prostate.

16. A method for resecting, coagulating or vaporizing tissue in a body organ, the method comprising:

introducing a surgical instrument comprising an elongate shaft having a proximal end and a distal end, an active electrode near the distal end, and a return electrode into a the body organ distended with an electrically conductive fluid to submerse both the active electrode and return electrode; and passing current between the active electrode and the return electrode while the active electrode is contacting the tissue, wherein the active electrode has a surface area which is selected to produce a current density sufficient to resect, coagulate or vaporize the tissue.

* * * * *